United States Patent
Kimura

(12) 
(10) Patent No.: US 6,548,528 B2
(45) Date of Patent: Apr. 15, 2003

(54) PESTICIDAL PYRAZOLES AND DERIVATIVES

(75) Inventor: Yasuo Kimura, Yokohama (JP)

(73) Assignee: Rhone-Poulenc Agro, Lyons (FR)

(*) Notice: Subject to any disclaimer, the term of this patent is extended or adjusted under 35 U.S.C. 154(b) by 0 days.

(21) Appl. No.: 10/155,106

(22) Filed: May 24, 2002

(65) Prior Publication Data

US 2002/0147225 A1 Oct. 10, 2002

Related U.S. Application Data

(62) Division of application No. 09/308,852, filed on Jul. 19, 1999, now Pat. No. 6,414,010.

(30) Foreign Application Priority Data

Nov. 29, 1996 (EP) .............................................. 96119152

(51) Int. Cl.$^7$ ............................................... A01N 43/56
(52) U.S. Cl. ...................... 514/404; 514/341; 514/407; 424/84; 424/405; 424/409; 424/410; 424/DIG. 11
(58) Field of Search ................................ 514/404, 341, 514/407; 424/405, 406, 407, 408, 409, 410, 84, DIG. 11

(56) References Cited

U.S. PATENT DOCUMENTS

| | | | |
|---|---|---|---|
| 3,624,953 A | 12/1971 | Crosby | 43/131 |
| 5,159,778 A | 11/1992 | Metzner et al. | 43/121 |
| 5,232,940 A | 8/1993 | Hatton et al. | 514/407 |
| 5,236,938 A | 8/1993 | Huang et al. | 514/341 |
| 5,347,749 A | 9/1994 | Chitwood et al. | 43/124 |
| 5,390,440 A | 2/1995 | Mihealsick | 43/124 |
| 5,801,189 A | 9/1998 | Twinn | 514/406 |
| 5,942,533 A | 8/1999 | Colliot | 514/407 |

FOREIGN PATENT DOCUMENTS

| | | |
|---|---|---|
| DE | 19511269 | 10/1995 |
| EP | 0 295 117 | 12/1988 |
| EP | 0 385 809 | 9/1990 |
| EP | 0 403 300 | 12/1990 |
| EP | 0 679 650 | 11/1995 |
| WO | 87/03781 | 7/1987 |
| WO | 91/03939 | 4/1991 |
| WO | 93/06089 | 4/1993 |
| WO | 94/21606 | 9/1994 |
| WO | 95/22902 | 8/1995 |
| WO | 96/29872 | 3/1996 |
| WO | 96/16544 | 6/1996 |
| WO | 96/31123 | 10/1996 |

OTHER PUBLICATIONS

"Les Termites Et La Protection Des Constructions," Cahiers Du Centre Scientifique Et Technique Du Batiment, No. 10, 4e Trimestre, Paris France, pp. 1–10 (1950).

Hamon et al, "Worldwide Development Of Fipronil Insecticide," Proceedings, Beltwide Cotton Conference, vol. 2, pp. 759–765 (1996).

Mariconi et al, "Ensaios De Combate AO Cupim De Monte Cornitermes Cumulans (Kollar, 1832) (Isoptera, Termitidae)," Field Tests For Control of the Mound–Building Termite Cormitermes Cumulins (Kollar, 1832) (Isoptera, Termitidae), Scientia Agricola, vol. 51, No. 3, pp. 505–508 (1994).

English language abstract of DE 19511269 (1995).
English language abstract of EP 0 679 650 (1995).

*Primary Examiner*—Neil S. Levy
(74) *Attorney, Agent, or Firm*—Connolly Bove Lodge and Hutz LLP

(57) ABSTRACT

Process for the protection of a building that has already been built or is going to be built, whereby an effective amount of an insecticidally active compound is spread around or under the said building at discrete locations. The insecticide may be an arylpyrazole.

9 Claims, No Drawings

PESTICIDAL PYRAZOLES AND DERIVATIVES

CROSS-REFERENCE TO RELATED APPLICATION

The present application is a divisional of, and claims the benefit of, U.S. patent application Ser. No. 09/308,852, which was filed on Jul. 19, 1999, now U.S. Pat. No. 6,414,010, in the name of Yasuo Kimura, and was entitled Pesticidal Pyrazoles and Derivatives. U.S. patent application Ser. No. 09/308,852 issued to U.S. Pat. No. 6,414,010 on Jul. 2, 2002.

An object of the instant invention is to protect a building that has already been built or is going to be built against crawling insects, especially against termites.

The insecticidal compounds of the family of the 1-arylpyrazoles are known to be active against termites.

Conventional termite control operators apply the chemical around or under the building or houses to form a barrier against termites invasion. However loopholes in the treatment may cause failure of protection of the houses.

Another system is to use a bait which contains an attractant for termites so as to force the termites to eat the bait and then to be killed by the active ingredient contained also in that bait.

An object of the invention is to provide an improved process of protection of houses.

Another object of the invention is to provide a treatment against termites which reduce the number of the call-back from house owners of treated houses.

An object of the instant invention is to protect the building with the minimum amount of insecticidally active ingredient.

Another object of the instant invention is to have a good level of protection of buildings against termites while reducing the amount of applied insecticide.

Another object of the instant invention is to reduce the need to treat directly the location where the termites are or are expected to be.

Another object of the instant invention is to provide a curative treatment with reduced need to find out the precise place of termites attacks.

Another object of the instant invention is to provide a curative treatment which is effective even when attacked parts are untreated.

Another object of the instant invention is to provide a curative treatment which is mainly a blind treatment with no checking of the attacked parts.

Another object of the instant invention is to provide a termite treatment functioning like an intangible trap.

Another object of the instant invention is to provide a termite treatment without barrier.

Another object of the instant invention is to provide a termite treatment which is mainly a soil treatment.

It has been found that these goals may be achieved by means of the process of the instant invention.

The present invention relates to a process for the protection of a building that has already been built or is going to be built, whereby an effective amount of an insecticidally active compound is spread around or under the building at discrete locations.

The insecticidally active material which can be used in the invention is an active ingredient which is active by contact (contact with species to be killed) and has no repellent effect on the insects, preferably no repellent effect on the insects to be killed.

A preferred class of active ingredient which can be used in the invention are the compounds without quick knockdown effect, or compounds able to produce a so-called secondary killing effect, that is to say an action of killing insects which have not been directly treated by mean of the said insecticide. Also preferred are the insecticides which are able to kill the termites of the termites nest when brought back by treated termites coming close to the house or building built or to be built.

In a practical point of view, the most preferred compounds are insecticides of the 1-arylpyrazole type, especially those having the formula (I)

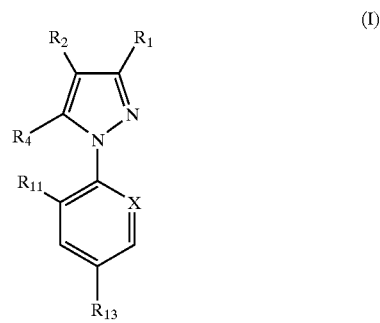

(I)

in which:

$R_1$ is CN or methyl or a halogen atom, $R_2$ is $S(O)_n R_3$ or 4,5-dicyanoimidazol 2-yl or haloalkyl, $R_3$ is alkyl or haloalkyl;

$R_4$ represents a hydrogen or halogen atom or a member of a group consisting of $NR_5R_6$, $S(O)_m R_7$, $C(O)R_7$, $C(O)O—R_7$, alkyl, haloalkyl, $OR_8$ and $—N=C(R_9)(R_{10})$;

$R_5$ and $R_6$ independently represent the hydrogen atom or an alkyl, haloalkyl, C(O)alkyl, alkoxycarbonyl or $S(O)_r CF_3$ radical; or $R_5$ and $R_6$ can together form a divalent alkylene radical which can be interrupted by one or two divalent heteroatoms, such as oxygen or sulfur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group which may optionally be unsubstituted or substituted by one or more halogen atoms or a member of the group consisting of OH, —O-alkyl, —S-alkyl, cyano, and alkyl;

$R_{11}$ and $R_{12}$ represent, independently of one another, a hydrogen or halogen atom, or CN or $NO_2$, $R_{13}$ represents a halogen atom or a haloalkyl, haloalkoxy, $S(O)_q CF_3$ or $SF_5$ group, X represents a trivalent nitrogen atom or a $C—R_{12}$ radical, the other three valences of the carbon atom forming part of the aromatic ring, m, n, q, and r represent, independently of one another, an integer equal to 0, 1, or 2, provided that, when $R_1$ is methyl, then either $R_3$ is haloalkyl, $R_4$ is $NH_2$, $R_{11}$ is Cl, $R_{13}$ is $CF_3$ and X is N; or then $R_2$ is 4,5-dicyanoimidazol 2-yl, $R_4$ is Cl, $R_{11}$ is Cl, $R_{13}$ is $CF_3$, and X is =C—Cl.

Alkyl groups have generally 1 to 6 carbon atoms.

A preferred group of effective 1-arylpyrazoles of the present invention is that wherein:

$R_1$ is CN; $R_3$ is a haloalkyl radical; $R_4$ is $NH_2$; X is C—$R_{12}$;

$R_{11}$ and $R_{12}$ represent, independently of one another, a halogen atom; and $R_{13}$ is a haloalkyl radical.

A most preferred compound is 5-amino 1-(2,6-dichloro 4-trifluoromethyl phenyl) 4-trifluoromethylsulfinyl 3-cyanopyrazole, hereafter designated as compound (A).

Compounds of formula (I) may be prepared according to known processes, for example as described in International Patent Publications n° WO 87/3781, 93/6089, and 94/21606 as well as in European Patent Applications 295117, 403300, 385809 or 679650. German Patent Publication 19511269 and U.S. Pat. Nos. 5,232,940 and 5,236,938 or other process according to the knowledge of a man skilled in the art of chemical synthesis, which is deemed to include the Chemical Abstract and the literature referred to therein. Compositions comprising the compounds of formula (I) may also be prepared according to the teaching of same prior art or similar one.

An advantageous way of practicing the invention is to use the active ingredient in a formulation which does not contain any adjuvant having termite attractant properties. Even though, such attractant may be used optionally, it may be risky, and it may make the residents or owners of the house reluctant against such treatment. Known processes were generally unable to avoid the use of attractant in order to be effective.

The process of the invention may be practiced in a preventive way as well as in a curative way.

The actual treatment by mean of active ingredient may be made inside or outside the outline of the houses or buildings to be built.

It is generally more effective to apply the active ingredient or formulation at a locus where the insects, especially the termites are more frequently crawling or traveling or climbing. These locus are more particularly the corners and/or crossing walls of the buildings or buildings which are going to be built. They are also more particularly the locus which have a greater humidity level than the rest of the perimeter of the house.

The active ingredient is applied advantageously on soil. It might be simple surface treatment or also spraying, mixing, blending or drenching of the soil with a formulation.

The effective amount of compound applied on soil is generally within the range of 0.05 g of active ingredient per $m^2$ of surface of the soil to 0.0001 $g/m^2$. This range is given for the precise locus where the active ingredient is applied.

As already said, the active ingredient is applied on discrete locus. The general rate of application is such that the treated part of the perimeter of the house is 0.5 to 7.5 treated meter per 10 meter of global perimeter, the width of treated locus being in the range of 1 to 50 cm, preferably 5 to 30 cm.

For their application, the compounds of the formula (I), or derivatives thereof, are generally in the form of compositions, which are in various solid or liquid forms.

Solid forms of compositions which can be used are dusting powders (with a content of the compound of formula (I), or a pesticidally acceptable salt thereof, ranging up to 80%), wettable powders or granules (including water dispersible granules), particularly those obtained by extrusion, compacting, impregnation of a granular carrier, or granulation starting from a powder (the content of the compound of formula (I), or a pesticidally acceptable salt thereof, in these wettable powders or granules being between about 0.5 and about 80%). Solid homogenous or heterogeneous compositions containing one or more compounds of formula (I), or pesticidally acceptable salts thereof, for example granules, pellets, briquettes or capsules, maybe used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilisers, surface-active agents, penetrating agents, corrosion inhibitors, colorants or adhesives. Emulsions of any required concentration, which are particularly suitable for application, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment for standing or running water.

All these aqueous dispersions or emulsions or spraying mixtures can be applied, by any suitable means, chiefly by spraying, at rates which are generally of the order of about 100 to about 1,200 liters of spraying mixture per hectare, but may be higher or lower (e.g. low or ultra-low volume) depending upon the need or application technique.

The concentrated suspensions, which can be applied by spraying, no are prepared so as to produce a stable fluid product which does not settle (fine grinding) and usually contain from about 10 to about 75% by weight of active ingredient, from about 0.5 to about 30% of surface active agents, from about 0.1 to about 10% of thixotropic agents, from about 0 to about 30% of suitable additives, such anti-foaming agents, corrosion inhibitors, stabilisers, penetrating agents, adhesives and, as the carrier, water or an organic liquid in which the active ingredient is poorly soluble or insoluble Some organic solids or inorganic salts may be dissolved in the carrier to help prevent settling or as antifreezes for water.

The wettable powders (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilisers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously for application.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

Generally speaking, the compositions for application against pests usually contain from about 0.00001% to about 95%, more particularly from about 0.0005% to about 50% by weight of one or more compounds of formula (I), or pesticidally acceptable salts thereof, or of total active ingredients The following examples are given to help the man skilled in the art to understand how to practice the invention. They should not be used to restrict or limit the said invention.

EXAMPLE 1

In an area where termites are passing or traveling, plans for a house are made. The plans are that the house will have a rectangular shape of 15 m×10 m with 4 rooms at the lower level.

Compound (A) is actually put on the soil at a rate of 0.01 g/m$^2$ of the soil at the location of the future corners of the house and at the crossing of the walls corresponding to each room according to the following scheme:

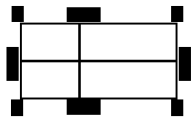

The treated area represents 5 m per 10 m of perimeter.

After 1 year after building the house, no attack of termite is observed.

A similar experiment made with chlorpyrifos results in the observation (one year after building the house) of a strong attack of termites (parts of the walls have holes of more than 10% of the volume).

EXAMPLE 2

Example 1 is repeated, except that the active ingredient is applied inside the perimeter of the house. In other words, the locus of application differ from example 1 only by the fact that it is located at the other side of the wall. Results similar to those of example 1 are obtained.

What is claimed is:

1. Process for the protection of a building against damage caused by insects comprising the steps of:
    a) forming a composition which is in solid form, wherein said composition comprises an insecticidally active ingredient, further wherein the amount of the active ingredient in the composition is from about 0.5 to about 80% by weight and the active ingredient has no quick knock down effect and a secondary killing action;
    b) forming treated and untreated locations along the perimeter of the building by applying an effective amount of said composition to discrete locations around or under said building along the perimeter of the building, wherein the treated locations are the discrete locations along the perimeter of the building where said composition has been applied and the untreated locations are the remaining portions of the perimeter where the composition was not applied;
    wherein the combination of said treated locations and said untreated locations along the perimeter of the building equal the total perimeter of the building and further wherein said treated locations make up 0.5 to 7.5 meter per 10 meter of the total perimeter of the building,
and said active ingredient is an insecticide of the formula (I)

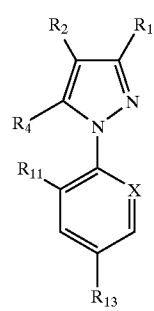

in which:
    $R_1$ is CN or methyl or a halogen atom,
    $R_2$ is $S(O)_nR_3$ or 4,5-dicyanoimidazol 2-yl or haloalkyl,
    $R_3$ is alkyl or haloalkyl;
    $R_4$ represents a hydrogen or halogen atom or a member of the group consisting of $NR_5R_6$, $S(O)_mR_7$, $C(O)R_7$, $C(O)O-R_7$, alkyl, haloalkyl, $OR_8$ and $-N=C(R_9)(R_{10})$;
    $R_5$ and $R_6$ together form a divalent alkylene radical which is interrupted by one or two divalent heteroatoms, said divalent heteroatoms being independently selected from the group consisting of oxygen and sulfur;
    $R_7$ represents an alkyl or haloalkyl radical;
    $R_8$ represents an alkyl or haloalkyl radical or a hydrogen atom;
    $R_9$ represents an alkyl radical or a hydrogen atom;
    $R_{10}$ represents a phenyl or heteroalkyl group which may optionally be unsubstituted or substituted by one or more halogen atoms or a member of the group consisting of OH, —O-alkyl, —S-alkyl, cyano, and alkyl;
    $R_{11}$ and $R_{12}$ represent, independently of one another, a hydrogen or halogen atom, or CN or $NO_2$,
    $R_{13}$ represents a halogen atom or a haloalkyl, haloalkoxy, $S(O)_qCF_3$ or $SF_5$ group,
    X represents a trivalent nitrogen atom or a C—$R_{12}$ radical, wherein the other three valences of the carbon atom are part of the aromatic ring,
    m, n, q, and r represent, independently of one another, an integer equal to 0, 1 or 2,
    provided that, when $R_1$ is methyl, then either $R_3$ is haloalkyl, $R_4$ is $NH_2$, $R_{11}$ is Cl, $R_{13}$ is $CF_3$ and X is N; or $R_2$ is 4,5-dicyanoimidazol 2-yl, $R_4$ is Cl, $R_{11}$ is Cl, $R_{13}$ is $CF_3$, and X is =C—Cl.

2. The process of claim 1, wherein said composition is in the form of a powder.

3. The process of claim 1, wherein said composition is in the form of granules.

4. The process of claim 1, wherein said composition is in the form of briquettes.

5. The process of claim 1, wherein said composition is in the form of pellets.

6. The process of claim 1, wherein said composition is in the form of capsules.

7. The process of claim 1, wherein said insecticidally active ingredient is 5-amino-1-(2,6-dichloro-4-trifluoromethyl phenyl)-4-trifluoromethylsulfinyl-3-cyanopyrazole.

8. The process of claim 1, wherein said composition comprises:

(a) from about 10 to about 80% by weight of said active ingredient;
(b) from about 20 to about 90% by weight of a solid carrier;
(c) from about 0 to about 5% by weight of a wetting agent;
(d) from about 3 to about 10% by weight of a dispersing agent; and
(e) from about 0 to about 80% by weight of one or more additives.

9. The process of claim 8, wherein said additives are selected from the group consisting of stabilizers, penetrating agents, adhesives, anti-caking agents and colorants.

* * * * *